United States Patent
Carle et al.

(10) Patent No.: US 11,883,524 B2
(45) Date of Patent: Jan. 30, 2024

(54) COSMETIC COMPOSITIONS

(71) Applicant: MARY KAY INC., Addison, TX (US)

(72) Inventors: Tiffany Carle, Addison, TX (US);
Milagros Sanchez, Addison, TX (US);
David Gan, Addison, TX (US)

(73) Assignee: MARY KAY INC., Addison, TX (US)

( * ) Notice: Subject to any disclaimer, the term of this patent is extended or adjusted under 35 U.S.C. 154(b) by 0 days.

(21) Appl. No.: 18/104,511

(22) Filed: Feb. 1, 2023

(65) Prior Publication Data
US 2023/0355505 A1    Nov. 9, 2023

Related U.S. Application Data

(63) Continuation of application No. 17/509,830, filed on Oct. 25, 2021, now Pat. No. 11,612,559, which is a continuation of application No. 16/706,290, filed on Dec. 6, 2019, now Pat. No. 11,185,492.

(60) Provisional application No. 62/780,036, filed on Dec. 14, 2018.

(51) Int. Cl.
| | | |
|---|---|---|
| *A61K 36/00* | (2006.01) | |
| *A61K 8/9789* | (2017.01) | |
| *A61K 8/06* | (2006.01) | |
| *A61K 8/11* | (2006.01) | |
| *A61K 8/67* | (2006.01) | |
| *A61Q 19/00* | (2006.01) | |
| *A61Q 19/08* | (2006.01) | |
| *A61K 8/44* | (2006.01) | |

(52) U.S. Cl.
CPC .............. *A61K 8/9789* (2017.08); *A61K 8/06* (2013.01); *A61K 8/11* (2013.01); *A61K 8/676* (2013.01); *A61K 8/678* (2013.01); *A61Q 19/007* (2013.01); *A61Q 19/08* (2013.01); *A61K 8/44* (2013.01); *A61K 2800/412* (2013.01); *A61K 2800/413* (2013.01)

(58) Field of Classification Search
CPC ....... A61Q 19/007; A61Q 19/08; A61Q 19/00
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 5,556,617 A | 9/1996 | Ribier et al. |
| 5,660,839 A | 8/1997 | Allec et al. |
| 6,184,247 B1 | 2/2001 | Schneider |
| 8,206,757 B2 | 6/2012 | McNeary |
| 8,999,408 B2 | 4/2015 | Antony |
| 9,044,404 B2 | 6/2015 | Mehta et al. |
| 9,254,276 B2 | 2/2016 | Li et al. |
| 9,918,931 B2 | 3/2018 | Dersh et al. |
| 2003/0199576 A1 | 10/2003 | Lee et al. |
| 2004/0109905 A1 | 6/2004 | Bagchi |
| 2005/0163880 A1 | 7/2005 | Pusateri et al. |
| 2005/0266092 A1 | 12/2005 | Viladot Petit et al. |
| 2006/0275229 A1* | 12/2006 | Pillai ............... A61K 8/671 424/59 |
| 2012/0015011 A1 | 1/2012 | Shim et al. |
| 2015/0297652 A1 | 10/2015 | Balaraman |
| 2017/0087082 A1 | 3/2017 | Doering et al. |

FOREIGN PATENT DOCUMENTS

| | | |
|---|---|---|
| CN | 103585052 | 2/2014 |
| CN | 104905996 | 9/2015 |
| CN | 106943310 | 7/2017 |
| CN | 108542823 | 9/2018 |
| EP | 1600210 | 11/2005 |
| KR | 20040003556 | 1/2004 |
| KR | 20110073495 | 6/2011 |
| KR | 20120130300 | 11/2012 |
| KR | 20130057542 | 6/2013 |
| KR | 20130132548 | 12/2013 |
| KR | 20140005204 | 1/2014 |
| KR | 20140071273 | 6/2014 |
| KR | 101627051 | 6/2016 |
| KR | 20160144785 | 12/2016 |
| WO | WO 2017134837 | 8/2017 |
| WO | WO 2018075810 | 4/2018 |
| WO | WO 2018163176 | 9/2018 |

OTHER PUBLICATIONS

"Hydrobrite" *GNPD*, retrieved from www.gripd.com, Dec. 29, 2011.
"Nourish Am/Pm Nourishment Cream" *GNPD*, retrieved from www.gripd.com, Aug. 4, 2011.
Chen, Qingxi. *Enzymology and the Research Technology.* Xiamen University Press, 2015, p. 221 (English Translation of relevant parts provided).
International Cosmetic Ingredient Dictionary and Handbook, 12th Edition (2008), vol. 1, p. 210.
International Cosmetic Ingredient Dictionary and Handbook, 12th Edition (2008), vol. 2, p. 2011.
International Cosmetic Ingredient Dictionary and Handbook, 12th Edition (2008), vol. 3. pp. 2738, 2775-2776, 2877.
International Search Report and Written Opinion issued in Corresponding PCT application no. PCT/US2019/065016, dated Mar. 26, 2020.

(Continued)

Primary Examiner — Qiuwen Mi
(74) Attorney, Agent, or Firm — NORTON ROSE FULBRIGHT US LLP

(57) ABSTRACT

Disclosed is a method of improving a condition or appearance of skin. The method can include applying to skin an effective amount of a topical skin composition comprising tetrahexyldecyl ascorbate, Phyllanthus emblica fruit extract, and tocopherol or tocopherol acetate.

9 Claims, 3 Drawing Sheets

(56) References Cited

OTHER PUBLICATIONS

Montenegro, Lucia "Nanocarriers for skin delivery of cosmetic antioxidants" *Journal of Pharmacy & Pharmacognosy Research* 2014, 2(4), 73-92.
Office Action and Search Report issued in Corresponding Chinese Application no. 201911293501.2, dated Jan. 19, 2023 (English Translation provided).
Chao et al. "Biochemistry" *China Science and Technology Press* 2017, p. 38 (English translation of relevant parts provided).
Office Action issued in Corresponding Chinese Application No. 201911293501.2, dated Jul. 12, 2023 (English Translation provided).
Wang et al., "Development and Application of Plant Additives in Cosmetics" *China Light Industry Press* 2013, p. 36 (English translation of relevant parts provided).
Wang, Xuemei. "If Up to Fashion Be Her Eyebrow Dyes—Cosmetics and Health Beauty" *Anhui University Press* 2004, p. 140 (English translation of relevant parts provided).
Chen, Wei. *Scientific Selection of Nutrition and Health Products*. China Light Industry Press, 2007, p. 64 (English Translation of relevant parts provided).
Decision on Rejection issued in Corresponding Chinese Application No. 201911293501.2, dated Nov. 24, 2023 (No English Translation provided).

\* cited by examiner

* indicates statistical significance *p*<0.05

COSMETIC COMPOSITIONS

CROSS REFERENCE TO RELATED APPLICATIONS

The present application is a continuation of U.S. patent application Ser. No. 17/509,830 filed Oct. 25, 2021, which is a continuation of U.S. patent application Ser. No. 16/706,290 filed Dec. 6, 2019 (now U.S. Pat. No. 11,185,492), which claims priority to U.S. Prov. App. No. 62/780,036 filed Dec. 14, 2018. The contents of the referenced applications are incorporated into the present application by reference.

BACKGROUND OF THE INVENTION

A. Field of the Invention

The present invention relates generally to topical skin compositions that can be used to improve skin conditions and skin appearance. In some aspects, the topical skin compositions are used for anti-ageing and moisturizing effect on the skin. In particular, the compositions were found to be able to inhibit matrix metalloproteinase enzyme activity, inhibit production of cyclooxygenase-1 (COX-1) and tyrosinase, and/or inhibit melanogenesis in skin, promote the synthesis of collagen, and/or lysyl oxidase in skin. The combination of ingredients of the compositions can include tetrahexyldecyl ascorbate, Phyllanthus emblica fruit extract, vegetable amino acids, ascorbic acid, optionally tocopherol, or combinations thereof.

B. Description of Related Art

Many factors contribute to skin aging such as the actual age of a person, the amount of exposure to environmental factors (e.g., sun light, pollution, chemicals, smoke, etc.), and how well a person has taken care of their skin. In particular, skin aging concerns two processes—intrinsic aging, which is related to the natural aging process and genetic influences, and extrinsic, or accumulated damage due to environmental factors such as sun exposure. This combination of factors eventually leads to visible signs of aging, and over time these signs progress through three stages—early, moderate and advanced.

The early signs of skin aging include the first stages of visible fine lines, especially around the eyes, and the beginning of uneven skin tone. Cell turnover begins to slow, and this can have a dulling effect on the complexion. Collagen and elastin—while still healthy—can start to suffer early damage, leaving skin slightly less resilient. If the matrix is left unprotected, wrinkles that are forming underneath the surface of the skin will eventually become more noticeable due to damage in the dermal layer. Eyes can occasionally look puffy, and pores appear slightly more noticeable. Typically, this occurs in an age range of about 25 to 35 years of age.

The moderate signs of skin aging include more pronounced expression lines around the eyes, the mouth and on the forehead. Underneath the eyes dark circles can become more noticeable. The skin's support structure becomes weaker as less collagen is produced, and elastin fibers begin to lose their ability to "snap" back. Skin loses vital moisture more easily, and dark spots can become more of an issue. Fine lines on the neck can become more visible, and "marionette" lines on either side of the mouth can begin to appear. More significant age spots begin to surface, eyes may look tired more often, and pores appear larger. This typically occurs in an age range of about 35 to 50 years of age.

The advanced signs of skin aging include "static" deep lines and wrinkles that are visible even when the face is at rest. The supporting structure of collagen and elastin is severely compromised and skin sagging, especially in the cheek and jawline areas, becomes evident. The neck shows signs of cumulative damage, with the skin becoming loose and marked by horizontal wrinkles called "tree rings." Dark spots become more prominent, and the eye area can show noticeable crepiness, sagging, puffiness and more pronounced dark circles in addition to a "drooping" upper eyelid. Skin loses its youthful volume and lift due to a loss of natural cushioning, and skin dryness is more pronounced as the external barrier is compromised, oil production slows and internal moisture levels drop. Cell turnover slows dramatically, and dead skin cells remain on the skin's surface which can dull the complexion and make pores more noticeable. The thickness of the skin is also impacted, and as it becomes thinner it's more easily irritated. Typically this occurs in an age range of above 50 years of age.

Skin dryness is another common skin issue. As the skin is the body's first line of defense against hazardous elements, skin dryness may not only cause an aesthetically displeasing look to skin but may also lead to itchiness, redness, blotches, irritation, and inflammation. It is essential and necessary to protect the skin from the elements and to treat dryness to avoid certain skin conditions.

Current products on the market either do not effectively address ageing skin and/or skin dryness, or have skin irritating effects. The inventors, however, have discovered a unique combination of ingredients that work in a symbiotic relationship with one another to effectively address the signs of early, moderate, and advanced skin ageing.

SUMMARY OF THE INVENTION

The inventors have identified a solution to at least some of the problems associated with current products to counteract some of the intrinsic and extrinsic factors that change the appearance and/or condition of skin and eventually cause skin ageing. The solution resides in a combination of ingredients including any possible combination of tetrahexyldecyl ascorbate, Phyllanthus emblica fruit extract, tocopherol, and/or ascorbic acid. The ingredients can further contain vegetable amino acids. The combination of ingredients can be used to create a topical skin composition to revitalize and rebuild the skin matrix by attacking and/or up regulating various biochemical pathways. These pathways may include inhibiting matrix metalloproteinase enzyme activity, inhibit production of cyclooxygenase-1 and/or tyrosinase, inhibiting melanogenesis in skin, and/or promoting the synthesis of collagen and/or lysyl oxidase in skin.

In embodiments of the invention, there is provided a topical skin composition. In some aspects, the topical skin composition may include any one of, any combination of, or all of tetrahexyldecyl ascorbate, Phyllanthus emblica fruit extract, ascorbic acid, and optionally tocopherol. The topical skin composition can further include vegetable amino acids. The amounts of the ingredients within the topical skin composition can vary (e.g., amounts can be as low as 0.000001% to as high as 98% w/w or any range therein). In some aspects, the topical skin composition can include 0.1 to 10% by weight of tetrahexyldecyl ascorbate and all ranges and values there between including 0.1 to 0.5%, 0.5 to 1.0%, 1.0 to 1.5%, 1.5 to 2.0%, 2.0 to 2.5%, 2.5 to 3.0%, 3.0 to 3.5%, 3.5 to 4.0%, 4.0 to 4.5%, 4.5 to 5.0%, 5.0 to 5.5%, 5.5 to 6.0%, 6.0 to 6.5%, 6.5 to 7.0%, 7.0 to 7.5%, 7.5 to 8.0%, 8.0 to 8.5%, 8.5 to 9.0%, 9.0 to 9.5%, and 9.5 to 10.0%. The topical skin composition can include 0.01 to 1.0% by weight of Phyllanthus emblica fruit extract and all ranges and values there between including ranges of 0.01 to 0.05%, 0.05 to 0.1%, 0.1 to 0.15%, 0.15 to 0.20%, 0.20 to 0.25%, 0.25 to 0.30%, 0.30 to 0.35%, 0.35 to 0.40%, 0.40 to 0.45%, 0.45 to 0.50%, 0.50 to 0.55%, 0.55 to 0.60%, 0.60 to 0.65%, 0.65 to 0.70%, 0.70 to 0.75%, 0.75 to 0.80%, 0.70 to 0.75%, 0.75 to 0.90%, 0.90 to 0.95%, and 0.95 to 1.0%. The topical skin composition can include 0.005 to 0.5% by weight of ascorbic acid and all ranges and values there between including ranges of 0.005 to 0.01%, 0.01 to 0.02%, 0.02 to 0.04%, 0.04 to 0.06%, 0.06 to 0.08%, 0.08 to 0.1%, 0.1 to 0.12%, 0.12 to 0.14%, 0.14 to 0.16%, 0.16 to 0.18%, 0.18 to 0.20%, 0.20 to 0.22%, 0.22 to 0.24%, 0.24 to 0.26%, 0.26 to 0.28%, 0.28 to 0.30%, 0.30 to 0.32%, 0.32 to 0.34%, 0.34 to 0.36%, 0.36 to 0.38%, 0.38 to 0.40%, 0.40 to 0.42%, 0.42 to 0.44%, 0.44 to 0.46%, 0.46 to 0.48%, and 0.48 to 0.50%. The topical skin composition can include 0.0001 to 0.01% by weight of tocopherol and all ranges and values there between including ranges of 0.0001 to 0.0005%, 0.0005 to 0.001%, 0.001% to 0.0015%, 0.0015% to 0.002%, 0.002% to 0.0025%, 0.0025% to 0.003%, 0.003% to 0.0035%, 0.0035% to 0.004%, 0.004% to 0.0045%, 0.0045% to 0.005%, 0.005% to 0.0055%, 0.0055% to 0.006%, 0.006% to 0.0065%, 0.0065% to 0.007%, 0.007% to 0.0075%, 0.0075% to 0.008%, 0.008% to 0.0085%, 0.0085% to 0.009%, 0.009% to 0.0095%, and 0.0095% to 0.01%. The topical skin composition can further include 0.03 to 3% by weight vegetable amino acids and all ranges and values there between including ranges of 0.03 to 0.06%, 0.06 to 0.09%, 0.09 to 0.12%, 0.12 to 0.15%, 0.15 to 0.18%, 0.18 to 0.21%, 0.21 to 0.24%, 0.24 to 0.27%, 0.27 to 0.30%, 0.30 to 0.45%, 0.45 to 0.60%, 0.60 to 0.75%, 0.75 to 0.90%, 0.90 to 1.0%, 1.0 to 1.2%, 1.2 to 1.4%, 1.4 to 1.6%, 1.6 to 1.8%, 1.8 to 2.0%, 2.0 to 2.2%, 2.2 to 2.4%, 2.4 to 2.6%, 2.6 to 2.8%, and 2.8 to 3.0%.

In some embodiments, the ascorbic acid and/or tocopherol are encapsulated. In some aspects, ascorbic acid may be encapsulated in nanospheres. In some aspects, the tocopherol may be encapsulated in microspheres. In some embodiments of the invention, the nanospheres encapsulating the ascorbic acid are surrounded by the microspheres encapsulating the tocopherol. In some aspects, the ascorbic acid-encapsulating nanospheres may be encapsulated within the microspheres that encapsulate tocopherol. In certain aspects, the ascorbic acid and tocopherol are encapsulated such that one or more ascorbic acid particles are disposed as a core portion that is encapsulated by a microsphere containing tocopherol. In some aspects, the encapsulation are configured for controlled release of ascorbic acid and tocopherol to the skin. The controlled release of ascorbic acid and tocopherol together may be capable of facilitating vitamin recycling process and extending an effective duration (life span) of tocopherol. In some aspects, the nanospheres may have an average diameter of 100 to 5000 nm and all ranges and values there between including ranges of 100 to 200 nm, 200 to 300 nm, 300 to 400 nm, 400 to 500 nm, 500 to 600 nm, 600 to 700 nm, 700 to 800 nm, 800 to 900 nm, 900 to 1000 nm, 1000 nm to 1500 nm, 1500 to 2000 nm, 2000 to 2500 nm, 2500 to 3000 nm, 3000 to 3500 nm, 3500 to 4000 nm, 4000 to 4500 nm, and 4500 to 5000 nm. The microspheres may have an average diameter of 20 to 100 μm and all ranges and values there between including 20 to 30 μm, 30 to 40 μm, 40 to 50 μm, 50 to 60 μm, 60 to 70 μm, 70 to 80 μm, 80 to 90 μm, and 90 to 100 μm. In some aspects, the nanospheres can comprise a hydrophobic material including one or more of natural wax, synthetic wax, vegetable wax, natural wax and silicon copolymer, synthetic wax and silicon copolymer, fatty acid esters, fatty alcohols, solid hydrogenated plant oil, natural polymers and synthetic polymers. In some instances, the hydrophobic material can include alkylated polyvinyl pyrrolidine, hydrogenated castor oil, hydrogenated vegetable oil, hard paraffin, hard fat and triglyceride, or combinations thereof. In some aspects, the microspheres can be formed of a moisture sensitive matrix material. In some instances, the moisture sensitive matrix material can include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethylaminoethyl ammonium functional groups, polyethylene oxides, water soluble polyamide or polyester, or combinations thereof. In some aspects, the microspheres can be dissolved to release the tocopherol and the nanospheres upon contact with moisture. In some aspects, the nanospheres can be dissolved to release ascorbic acid upon contact with moisture.

In some aspects, the topical skin composition can comprise an effective amount of tetrahexyldecyl ascorbate to inhibit matrix metalloproteinase enzyme activity. The matrix metalloproteinase enzyme may comprise MMP3. In some embodiments, the topical skin composition may comprise an effective amount of tetrahexyldecyl ascorbate and/or Phyllanthus emblica fruit extract to stimulate collagen production in skin. In some embodiments, the topical skin composition may comprise an effective amount of vegetable amino acids to inhibit tyrosinase in skin. In some embodiments, the topical skin composition may comprise an effective amount of Phyllanthus emblica fruit extract to inhibit cyclooxygenase-1 in skin. In some embodiments of the invention, the topical skin composition may comprise an effective amount of Phyllanthus emblica fruit extract to stimulate lysyl oxidase activity in skin. In some embodiments, the topical skin composition may comprise an effective amount vegetable amino acids to inhibit melanogenesis in skin.

In some aspects, the Phyllanthus emblica fruit extract can be an aqueous extract of Phyllanthus emblica fruits. In some aspects, the vegetable amino acids are extracted from navy bean plants. In some aspects, the topical skin composition can be an emulsion, a serum, a gel emulsion, or a gel serum. In some aspects, the topical skin composition is a polymeric emulsion. In some aspects, the topical skin composition is effective to reduce a skin condition comprising photo damage, loss of facial firmness, fine lines, deep lines, wrinkles, skin dullness, dry skin, age spots, or combination thereof.

In some instances, the extracts can be aqueous extracts. By aqueous extracts, it is meant that an aqueous solution can be used as the extractant or solvent to obtain the extract. The aqueous extracts can be in liquid form or in powdered form. However, in some other instances, other solvents such as alcohols, glycols, hydro-alcoholic, and/or hydroglycolic extracts can be used. In some instances, the composition further comprises water. In some instances, the composition includes 25% to 98% by weight of water.

In some aspects, the topical skin compositions may further include a sunscreen reagent. The compositions can be sunscreen lotions, sprays, or creams. Non-limiting example for the sun screen reagent may include but are not limited to octinoxate, zinc oxide, ethylhexyl salicylate, ensulizole, homosalate, avobenzone, octocrylene, oxybenzone, or combinations thereof. In some instances, the topical skin composition may have a sun protection factor (SPF) in a range of 2 to 100 and all ranges and values there between such as SPF 2, SPF 15, SPF 25, SPF 30, SPF 35, SPF 40, SPF 50, SPF 60, SPF 70, SPF 75, SPF 80, SPF 90 and SPF 100. In some aspects, the topical skin compositions may exclude a sunscreen agent.

The topical skin compositions can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In some aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference. The topical skin composition can be formulated as a mask, lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The topical skin composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben. In some embodiments, the composition is paraben-free.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

In some embodiments of the invention, there is disclosed a method of improving a condition or appearance of skin. The method may comprise applying to the skin an effective amount of a topical skin composition that comprises tetrahexyldecyl ascorbate, Phyllanthus emblica fruit extract, tocopherol, ascorbic acid, or combinations thereof. In some aspects, the topical skin composition can further include vegetable amino acids. In some aspects, the ascorbic acid and/or tocopherol are encapsulated. The encapsulation can be in nanospheres or microspheres configured for controlled release of ascorbic acid and tocopherol to the skin. The controlled release of ascorbic acid and tocopherol together may be capable of facilitating vitamin recycling process and extending an effective duration (life span) of tocopherol. In certain aspects, the ascorbic acid and tocopherol may be encapsulated such that one or more ascorbic acid particles are disposed as a core portion that is encapsulated by a microsphere containing tocopherol. In some aspects, the ascorbic acid may be encapsulated in nanospheres. The tocopherol may be encapsulated in microspheres. In some aspects, the nanospheres encapsulating the ascorbic acid are encapsulated in the microspheres such that the ascorbic acid-encapsulating nanospheres are surrounded by the microspheres encapsulating tocopherol.

In some aspects, by applying the topical skin composition, the skin may be treated to improve a skin condition comprising skin radiance, skin tone clarity, skin brightness, skin tone evenness, or combinations thereof. In some aspects, by applying the topical skin composition, the skin may be treated to reduce a skin condition comprising photo damage, loss of facial firmness, fine lines, deep lines, wrinkles, skin dullness, skin sagging, appearance of age spots on skin, or combinations thereof. In some aspects, the skin may be treated to increase moisture level thereof. In some aspects, the skin moisture level may be increased within about 15 minutes of applying the topical skin composition.

In some aspects, by applying the topical skin composition, the skin is treated to inhibit matrix metalloproteinase enzyme activity. In some aspects, the matrix metalloproteinase enzyme may include MMP3. In some aspects, by applying the topical skin composition, the skin may be treated to stimulate production of matrix proteins comprising collagen and/or lysyl oxidase. In some aspects, by applying the topical skin composition, the skin is treated to inhibit production of cyclooxygenase-1 and/or tyrosinase. In some aspects, by applying the topical skin composition, the skin may be treated to inhibit melanogenesis. In some aspects, the Phyllanthus emblica fruit extract may be an aqueous extract from Phyllanthus emblica fruits. In some aspects, the vegetable amino acids may be from navy bean plants. In some aspects, the topical skin composition can be an emulsion, a serum, a gel, a gel emulsion, or a gel serum. In some aspects, the topical skin composition may be a polymeric emulsion.

In some aspects, the topical skin composition can be applied to a fine line, a wrinkle, an age spot, or a deep line on the skin. In some aspects, the topical skin composition can be applied to sagging skin or non-elastic skin. In some aspects, the composition can be applied to the periorbital region and/or the crow's feet region of the skin. In some aspects, the topical skin composition can be applied to facial skin or neck skin. In some aspects, the composition remains on the skin for at least 30 minutes. In some aspects, the topical skin composition can be applied one or more times daily for at least 4 weeks.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a toner, a sunscreen, a mask, an anti-aging product, a deodorant, an antiperspirant, a perfume, a cologne, etc.

Also disclosed is a method of tightening or toning skin comprising topically applying to skin in need thereof a composition comprising any one of the compositions of the present invention, wherein topical application of said composition to skin tightens or tones said skin. The compositions disclosed above and throughout this specification can be used.

Also disclosed is a method of increasing the integrity of the dermal-epidermal junction ("DEJ") comprising topically applying any one of the combination of ingredients or compositions having said combinations disclosed throughout this specification to skin. This method can stimulate the production of proteins and enzymes in dermal and epidermal cells that aid in connecting the dermal layer to the epidermal layer. Not wishing to be bound by theory, it is believed that the combination of ingredients disclosed throughout the specification (e.g., tetrahexyldecyl ascorbate, Phyllanthus emblica fruit extract, vegetable amino acids, tocopherol, and/or ascorbic acid,) stimulate proteins that are vital to the health of the DEJ (e.g., collagen, and lysyl oxidase).

An additional embodiment includes an injectably acceptable solution comprising any one of the aforementioned combination of ingredients. An injectably acceptable solution includes a solution that can be safely injected into a human or animal.

It is also contemplated that compositions of the present invention can be included into food-based products (e.g., beverages, fortified water, energy drinks, nutritional drinks, solid foods, vitamins, supplements, etc.) and pharmaceutical products (e.g., pills, injectable solutions, drugs, etc.). "Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In the context of the present invention, at least the following 40 aspects are described. Aspect 1 includes a method of improving a condition or appearance of skin. The method comprises applying to the skin an effective amount of a topical skin composition comprising tetrahexyldecyl ascorbate, Phyllanthus emblica fruit extract, ascorbic acid, and optionally tocopherol.

Aspect 2 is dependent on aspect 1, wherein the topical skin composition further comprises vegetable amino acids.

Aspect 3 is dependent on aspect 2, wherein, by applying the topical skin composition, the skin is treated to inhibit melanogenesis and/or tyrosinase.

Aspect 4 is dependent on aspects 1 to 3, wherein the ascorbic acid and/or tocopherol are encapsulated in microspheres and/or nanospheres configured for controlled release of ascorbic acid and tocopherol.

Aspect 5 is dependent on aspect 4, wherein the ascorbic acid is encapsulated in nanospheres and tocopherol is encapsulated in microspheres.

Aspect 6 is dependent on aspect 5, wherein the nanospheres encapsulating the ascorbic acid are surrounded by microspheres encapsulating the tocopherol.

Aspect 7 is dependent on aspect 4, wherein the ascorbic acid and tocopherol are encapsulated such that one or more ascorbic acid particles are disposed as a core portion that is encapsulated by a microsphere containing tocopherol.

Aspect 8 is dependent on aspects 1 to 7, wherein, by applying the topical skin composition, the skin is treated to improve a skin condition comprising skin radiance, skin tone clarity, skin brightness, skin tone evenness, or combinations thereof Aspect 9 is dependent on aspects 1 to 8, wherein, by applying the topical skin composition, the skin is treated to reduce a skin condition comprising photo damage, loss of facial firmness, fine lines, deep lines, wrinkles, skin dullness, skin sagging, appearance of age spots on skin, or combinations thereof.

Aspect 10 is dependent on aspects 1 to 9, wherein, by applying the topical skin composition, the skin is treated to increase moisture level thereof.

Aspect 11 is dependent on aspect 10, wherein, by applying the topical skin composition, the skin moisture level is increased within about 15 minutes of applying the topical skin composition.

Aspect 12 is dependent on aspects 1 and 11, wherein, by applying the topical skin composition, the skin is treated to inhibit matrix metalloproteinase enzyme activity.

Aspect 13 is dependent on aspect 12, wherein the matrix metalloproteinase enzyme includes MMP3.

Aspect 14 is dependent on aspects 1 to 13, wherein, by applying the topical skin composition, the skin is treated to stimulate production of matrix proteins that comprise collagen, and/or lysyl oxidase.

Aspect 15 is dependent on aspects 1 to 14, wherein, by applying the topical skin composition, the skin is treated to inhibit production of cyclooxygenase-1.

Aspect 16 is dependent on aspects 1 to 15, wherein the topical skin composition further comprises water.

Aspect 17 is dependent on aspects 1 to 16, wherein the Phyllanthus emblica fruit extract is an aqueous extract from Phyllanthus emblica fruit.

Aspect 18 is dependent on aspects 1 to 17, wherein the topical skin composition is an emulsion, a serum, a gel, a gel emulsion, or a gel serum.

Aspect 19 is dependent on aspects 1 to 18, wherein the topical skin composition is a polymeric emulsion.

Aspect 20 is dependent on aspects 1 to 19, wherein the topical skin composition is applied to a fine line, a wrinkle, an age spot, or a deep line on the skin.

Aspect 21 is dependent on aspects 1 to 20, wherein the topical skin composition is applied to sagging skin or non-elastic skin.

Aspect 22 is dependent on aspects 1 to 21, wherein the topical skin composition is applied to the periorbital region and/or the crow's feet region of the skin.

Aspect 23 is dependent on aspects 1 to 22, wherein the topical skin composition is applied to facial skin or neck skin.

Aspects 24 is dependent on aspects 1 to 23, wherein, after topical application, the topical skin composition remains on the skin for at least 30 minutes.

Aspects 25 is dependent on aspects 1 to 24, wherein the topical skin composition is applied one or more times daily for at least 4 weeks.

Aspect 26 includes a topical skin composition comprising tetrahexyldecyl ascorbate, Phyllanthus emblica fruit extract, ascorbic acid, and optionally tocopherol.

Aspect 27 is dependent on aspect 26, wherein the topical skin composition comprises an effective amount of tetrahexyldecyl ascorbate, and/or Phyllanthus emblica fruit extract to stimulate production of collagen.

Aspect 28 is dependent on aspects 26 and 27, wherein the topical skin composition comprises an effective amount of tetrahexyldecyl ascorbate to inhibit matrix metalloproteinase enzyme activity.

Aspect 29 is dependent on aspect 28, wherein the matrix metalloproteinase enzyme comprises MMP3.

Aspect 30 is dependent on aspects 26 to 29, wherein the topical skin composition further comprises an effective amount of vegetable amino acids to inhibit tyrosinase and/or melanogenesis.

Aspect 31 is dependent on aspects 26 to 30, wherein the topical skin composition comprises an effective amount of Phyllanthus emblica fruit extract to inhibit cyclooxygenase-1.

Aspect 32 is dependent on aspects 26 to 31, wherein the topical skin composition comprises an effective amount of Phyllanthus emblica fruit extract to stimulate lysyl oxidase activity.

Aspect 33 is dependent on aspects 26 to 32, wherein the Phyllanthus emblica fruit extract is an aqueous extract of Phyllanthus emblica fruits.

Aspect 34 is dependent on aspects 26 to 33, wherein the ascorbic acid and/or tocopherol are encapsulated by nanospheres and microspheres configured for controlled release of ascorbic acid and tocopherol to the skin.

Aspect 35 is dependent on aspect 34, wherein the ascorbic acid is encapsulated in nanospheres and tocopherol is encapsulated in microspheres.

Aspect 36 is dependent on aspect 35, wherein the nanospheres containing the ascorbic acid are surrounded by microspheres containing the tocopherol.

Aspect 37 is dependent on aspect 34, wherein the ascorbic acid and tocopherol are encapsulated such that one or more ascorbic acid particles are disposed as a core portion that is encapsulated by a microsphere containing tocopherol.

Aspect 38 is dependent on aspects 26 to 37, wherein the vegetable amino acids are extracted from navy bean plants.

Aspect 39 is dependent on aspects 26 to 38, wherein the topical skin composition comprises 0.1 to 10 wt.% tetrahexyldecyl ascorbate, 0.01 to 1.0 wt.% Phyllanthus emblica fruit extract, 0.03 to 3 wt.% vegetable amino acids, 0.005 to 0.5 wt.% ascorbic acid, 0.0001 to 0.01 wt.% tocopherol, or combinations thereof Aspect 40 is dependent on aspects 26 to 39, wherein the topical skin composition is an emulsion, a serum, a gel, a gel emulsion, or a gel serum.

Aspect 41 is dependent on aspects 26 to 40, wherein the topical skin composition is polymeric emulsion.

Aspect 42 is dependent on aspects 26 to 41, wherein the topical skin composition is effective to reduce a skin condition comprising photo damage, loss of facial firmness, fine lines, deep lines, wrinkles, skin dullness, dry skin, age spots, or combinations thereof.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to promote or increase the production of collagen and/or oxidase, and/or inhibit matrix metalloproteinase enzyme activity, production of COX-1, and tyrosinase, and/or inhibit melanogenesis in skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
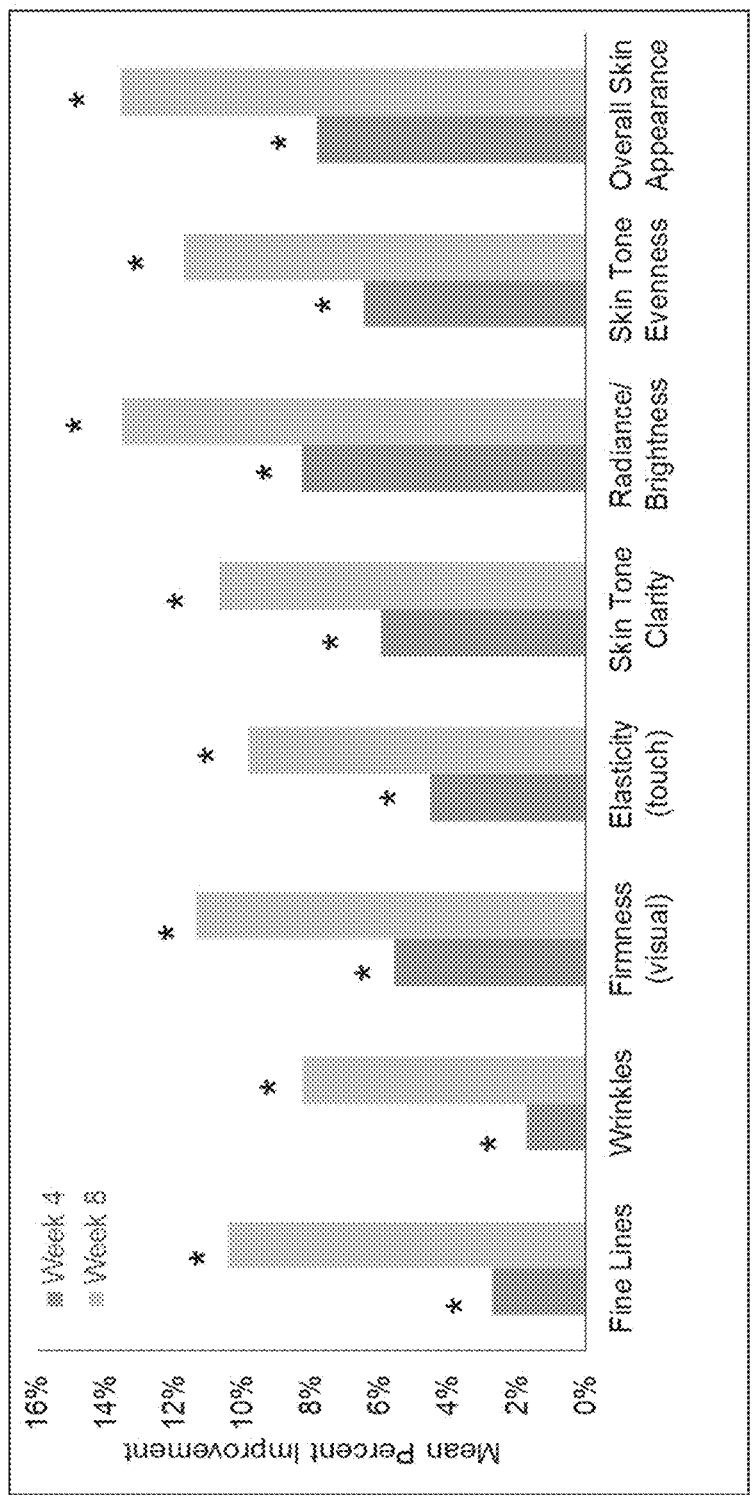
FIG. 1 shows a bar chart of the grading results from clinical expert on fine lines, wrinkles, firmness, elasticity, skin tone clarity, skin radiance/brightness, skin tone evenness, and overall skin photo-damage/appearance of tested subjects after using a serum comprising the combination of the skin active ingredients of the present invention for 4 and 8 weeks.

As noted above, the present invention provides a solution to the problems associated with skin ageing, sagging skin, wrinkles on the skin, and dry skin. The solution is premised on combinations of extracts and other compounds to inhibit production of COX-1, and/or tyrosinase in skin, inhibit the matrix metalloproteinase enzyme activity in skin, inhibit melanogenesis in skin, promote the synthesis of collagen and/or promote the activity of lysyl oxidase in skin. The combinations of extracts and compound can include tetrahexyldecyl ascorbate, Phyllanthus emblica fruit extract, vegetable amino acids, tocopherol, ascorbic acid, or any combination thereof.

These and other non-limiting aspects of the present invention are described in the following sections.

A. Active Ingredients

The present invention is premised on a determination that a combination of active ingredients—tetrahexyldecyl ascorbate, Phyllanthus emblica fruit extract, vegetable amino acids, tocopherol, ascorbic acid, or any combination thereof—can be used to improve skin's visual appearance, skin aging, sagging skin, and wrinkles on skin. More particularly, the combinations can reduce production of tyrosinase and/or COX-1 in skin, inhibit matrix metalloproteinase enzyme activity and/or melanogenesis in skin, promote the synthesis of collagen, and/or promote the lysyl oxidase activity in skin.

The combinations of ingredients can be used in different products to treat various skin conditions. By way of non-limiting examples, the combinations of ingredients can be formulated in an emulsion (e.g. oil in water, water in oil), a gel (e.g. silicon in water gel), a serum, a gel emulsion, a gel serum, a lotion, a mask, or a body butter.

Tetrahexyldecyl ascorbate, also known as ascorbyl tetraisopalmitate, is a vitamin C derivative that can function as an antioxidant and skin conditioner agent. Tetrahexyldecyl ascorbate can be a modified ascorbic acid derivative with enhanced absorption into lipid layers of skin. In some instances, tetrahexyldecyl ascorbate is supplied by Barnet under the trade name BV-OSC™.

Phyllanthus emblica fruit extract can be an aqueous extract of Phyllanthus emblica fruits. Phyllanthus emblica fruit, also known as amla, is a fruit of deciduous tree of Euphorbiaceae family. Phyllanthus emblica fruit extract contains vitamin C. In some aspects, the Phyllanthus emblica fruit extract can be extracted by macerating the fruit, which does not damage the plant constitutes, resulting in an ideal extract for cosmetic use. The Phyllanthus emblica (alma) tree may grow in Himalayas, over four thousand feet above sea level. In some aspects, the Phyllanthus emblica can be a source of Flavonoids, Apigenin, Gallic Acid, Ellagic Acid, Quercetin, Vitamin C, Amino Acides, Copper, Zinc, and Chromium. In some instances, the Phyllanthus emblica fruit extract can be supplied by Carrubba Inc.

Vegetable amino acids comprises amino acids, which are biological organic compounds composed of amine and carboxylic acid functional groups, along with a side-chain specific to each amino acid. In some aspects, the vegetable amino acids are extracted from navy bean plants. In some instances, the vegetable amino acids can be supplied by Carrubba Inc. under the tradename Navy Bean.

Ascorbic acid, also known as vitamin C, can be an antioxidant and an essential compound to maintain healthy connective tissue. Ascorbic acid can support skin's natural repair process. In some aspects, ascorbic acid can stimulate formation of collagen, which is a critical building block of skin.

Tocopherol, also known as vitamin E group, can be used as an antioxidant for limiting oxidative damage to skin. The vitamin E group can comprise α-tocopherol, β-tocopherol, and δ-tocopherol.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., Stevia rebaudiana (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers and/or reflectors (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., Aloe vera, chamomile, cucumber extract, Ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, saccharide isomerate, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, Aloe barbadensis, Aloe barbadensis extract, Aloe barbadensis gel, Althea officinalis extract, apricot (Prunus armeniaca) kernel oil, arginine, arginine aspartate, Arnica montana extract, aspartic acid, avocado (Persea gratissima) oil, barrier sphingolipids, butyl alcohol, beeswax, behenyl alcohol, beta-sitosterol, birch (Betula alba) bark extract, borage (Borago officinalis) extract, butcherbroom (Ruscus aculeatus) extract, butylene glycol, Calendula officinalis extract, Calendula officinalis oil, candelilla (Euphorbia cerifera) wax, canola oil, caprylic/capric triglyceride, cardamom (Elettaria cardamomum) oil, carnauba (Copernicia cerifera) wax, carrot (Daucus carota sativa) oil, castor (Ricinus communis) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (Anthemis nobilis) oil, cholesterol, cholesterol esters, cholesteryl hydroxystearate, citric acid, clary (Salvia sclarea) oil, cocoa (Theobroma cacao) butter, coco-caprylate/caprate, coconut (Cocos nucifera) oil, collagen, collagen amino acids, corn (Zea mays) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, Eucalyptus globulus oil, evening primrose (Oenothera biennis) oil, fatty acids, Geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (Vitis vinifera) seed oil, hazel (Corylus americana) nut oil, hazel (Corylus avellana) nut oil, hexylene glycol, hyaluronic acid, hybrid safflower (Carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (Jasminum officinale) oil, jojoba (Buxus chinensis) oil, kelp, kukui (Aleurites moluccana) nut oil, lactamide MEA, laneth-16, laneth-10 acetate, lanolin, lanolin acid, lanolin alcohol, lanolin oil, lanolin wax, lavender (Lavandula angustifolia) oil, lecithin, lemon (Citrus medica limonum) oil, linoleic acid, linolenic acid, Macadamia ternifolia nut oil, maltitol, matricaria (Chamomilla recutita) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (Olea europaea) oil, orange (Citrus aurantium dulcis) oil, palm (Elaeis guineensis) oil, palmitic acid, pantethine, panthenol, panthenyl ethyl ether, paraffin, PCA, peach (Prunus persica) kernel oil, peanut (Arachis hypogaea) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (Mentha piperita) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (Oryza sativa) bran oil, RNA, rosemary (Rosmarinus officinalis) oil, rose oil, safflower (Carthamus tinctorius) oil, sage (Salvia officinalis) oil, sandalwood (Santalum album) oil, serine, serum protein, sesame (Sesamum indicum) oil, shea butter (Butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (Glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (Helianthus annuus) seed oil, sweet almond (Prunus amygdalus dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (Triticum vulgare) germ oil, and ylang ylang (Cananga odorata) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the—Si-O—chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich.. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich..

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyl-taurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660 ; 4,849,484; 4,835, 206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof j. Preservatives Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof 2. Pharmaceutical Ingredients Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

G. Example

1. Example 1

Tables 1 and 2 describe generic formulations or skin testing formulations in which an active ingredient can be incorporated into. These formulations can also be used to determine the types of skin benefits that can be attributed to the active ingredient. These formulations are prepared in such a manner that any resulting skin benefit from topical application of the formula to skin can be directly attributed to the active ingredient being tested. In the context of aspects of the present invention, the active ingredient that can be used in the formulation may include tetrahexyldecyl ascorbate, Phyllanthus emblica fruit extract, vegetable amino acids, tocopherol, ascorbic acid, or all of such active ingredients, or at least 1, 2, 3, 4, and/or 5 of such active ingredients. It should be recognized that other standard testing vehicles can also be used to determine the skin benefit properties of active ingredient and that the following formulations are non-limiting testing vehicles.

TABLE 1*

| Ingredient | % Concentration (by weight) |
|---|---|
| Phase A | |
| Water | 84.80 |
| Xanthan gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |

TABLE 1*-continued

| Ingredient | % Concentration (by weight) |
|---|---|
| Phase C | |
| Active Ingredient** | 2.0 |
| TOTAL | 100 |

*Procedure for making composition: Sprinkle Xanthan gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

TABLE 2*

| Ingredient | % Concentration (by weight) |
|---|---|
| Phase A | |
| Water | 78.6 |
| M-paraben | 0.2 |
| P-paraben | 0.1 |
| Na$_2$ EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient** | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The active ingredients identified throughout this specification can be incorporated into composition as the active ingredient. The active ingredients can be individually used or combined in this composition. The concentration ranges of the active ingredients (or combination of active ingredients) can be modified as desired or needed by increasing or decreasing the amount of water.

2. Example 2

Formulations having combinations of active ingredients disclosed herein were prepared as topical skin and/or hair compositions. The formulation in each of Tables 3 to 6 was prepared as a polymeric serum.

TABLE 3*

| Ingredient | % Concentration (by weight) |
|---|---|
| Tetrahexyldecyl ascorbate | 1.6 |
| *Phyllanthus emblica* fruit extract | 0.11 |
| Vegetable amino acids | 0.30 |
| Tocopherol | 0.00315 |
| Ascorbic acid | 0.0469 |
| Water | 73.286 |
| Glycerin | 7.25 |
| Dimethicone | 4.6 |
| Hydrogenated polydecene | 4.5 |
| Butylene Glycol | 1.6 |
| Pentylene glycol | 1.2 |
| Betaine | 1.0 |
| Denatured alcohol (or alcohol) | 0.67 |
| Titanium dioxide | 0.59 |
| PEG-32 | 0.50 |

TABLE 3*-continued

| Ingredient | % Concentration (by weight) |
|---|---|
| Phenoxyethanol | 0.45 |
| MICA | 0.40 |
| Polyacrylamide | 0.40 |
| Triethanolamine | 0.32 |
| Acrylates/C10-30 alkyl acrylate crosspolymer | 0.25 |
| C13-14 Isoparaffin | 0.20 |
| Disodium EDTA | 0.20 |
| Fragrance/Parfum | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 40 to 75% w/w.

TABLE 4*

| Ingredient | % Concentration (by weight) |
|---|---|
| Tetrahexyldecyl ascorbate | 1.6 |
| *Phyllanthus emblica* fruit extract | 0.11 |
| Vegetable amino acids | 0.30 |
| Tocopherol | 0.00317 |
| Ascorbic acid | 0.0469 |
| Water | 72.936 |
| Glycerin | 7.25 |
| Dimethicone | 4.6 |
| Hydrogenated polydecene | 4.5 |
| Butylene Glycol | 1.6 |
| Pentylene glycol | 1.2 |
| Betaine | 1.0 |
| Phenoxyethanol | 0.765 |
| Denatured alcohol (or alcohol) | 0.674 |
| Titanium dioxide | 0.59 |
| PEG-32 | 0.50 |
| MICA | 0.40 |
| Polyacrylamide | 0.40 |
| Triethanolamine | 0.32 |
| Acrylates/C10-30 alkyl acrylate crosspolymer | 0.25 |
| C13-14 Isoparaffin | 0.20 |
| Disodium EDTA | 0.20 |
| Fragrance/Parfum | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 40 to 75% w/w.

TABLE 5*

| Ingredient | % Concentration (by weight) |
|---|---|
| Tetrahexyldecyl ascorbate | 1.6 |
| *Phyllanthus emblica* fruit extract | 0.11 |
| Vegetable amino acids | 0.30 |
| Tocopherol | 0.00315 |
| Ascorbic acid | 0.0469 |
| Water | 73.285 |
| Glycerin | 7.25 |
| Dimethicone | 4.6 |
| Hydrogenated polydecene | 4.5 |
| Butylene Glycol | 1.6 |
| Pentylene glycol | 1.2 |
| Betaine | 1.0 |
| Denatured alcohol (or alcohol) | 0.67 |
| Titanium dioxide | 0.59 |
| PEG-32 | 0.50 |
| Phenoxyethanol | 0.45 |
| MICA | 0.40 |
| Polyacrylamide | 0.40 |
| Triethanolamine | 0.32 |
| Acrylates/C10-30 alkyl acrylate crosspolymer | 0.25 |
| C13-14 Isoparaffin | 0.20 |
| Disodium EDTA | 0.20 |
| Fragrance/Parfum | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 40 to 75% w/w.

TABLE 6*

| Ingredient | % Concentration (by weight) |
|---|---|
| Tetrahexyldecyl ascorbate | 1.6 |
| *Phyllanthus emblica* fruit extract | 0.11 |
| Vegetable amino acids | 0.30 |
| Tocopherol | 0.00315 |
| Ascorbic acid | 0.0469 |
| *Optunia tuna* fruit extract | 0.0005 |
| Water | 73.260 |
| Glycerin | 7.27 |
| Dimethicone | 4.6 |
| Hydrogenated polydecene | 4.5 |
| Butylene Glycol | 1.6 |
| Pentylene glycol | 1.2 |
| Betaine | 1.0 |
| Alcohol | 0.67 |
| Titanium dioxide | 0.59 |
| PEG-32 | 0.50 |
| Phenoxyethanol | 0.45 |
| MICA | 0.403 |
| Polyacrylamide | 0.40 |
| Triethanolamine | 0.32 |
| Acrylates/C10-30 alkyl acrylate crosspolymer | 0.25 |
| C13-14 Isoparaffin | 0.20 |
| Disodium EDTA | 0.20 |
| Fragrance/Parfum | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 35% w/w, and preferably between 40 to 75% w/w.

3. Example 3 (In Vitro Efficacy of Ingredients)

The efficacy of the ingredients were determined by the following methods. The following are non-limiting assays that can be used in the context of the present invention. It should be recognized that other testing procedures can be used, including, for example, objective and subjective procedures.

It was determined that tetrahexyldecyl ascorbate stimulates collagen production and inhibits activity of MMP3. It was also determined that Phyllanthus emblica fruit extract stimulates collagen production and lysyl oxidase activity, and inhibits COX-1 level. It was also determined that Phyllanthus emblica fruit extract shows antioxidant capacity. It was also determined that vegetable amino acids inhibits B16 melanogenesis and mushroom tyrosinase. A summary of quantitative results is found in Table 7 and the methods used to determine the properties of the ingredients are provided below.

TABLE 7

Summary of results for in vitro test

| Assay | Ingredient | Activity |
| --- | --- | --- |
| Increase of collagen | Tetrahexyldecyl ascorbate | +50% |
|  | Phyllanthus emblica fruit extract | +15% |
| Inhibition of MMP3 activity | Tetrahexyldecyl ascorbate | −38% |
| Inhibition of mushroom tyrosinase | Vegetable amino acids | −39% |
| Inhibition of COX-1 | Phyllanthus emblica fruit extract | −56% |
| Increase of lysyl oxidase activity | Phyllanthus emblica fruit extract | +40% |
| Inhibition of B16 melanogenesis | Vegetable amino acids | −30% |
| Antioxidant Capacity | Phyllanthus emblica fruit extract |  |

Inhibition of Matrix Metalloproteinase Enzyme Activity (MMP3) Assay: MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay was designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond was replaced by a thioester bond in the thiopeptide. Hydrolysis of this bond by an MMP produced a sulfhydryl group, which reacted with DTNB [5,5'-dithiobis(2-nitrobenzoic acid), Ellman's reagent] to form 2-nitro-5-thiobenzoic acid, which was detected by its absorbance at 412 nm ($\varepsilon$=13,600 M-1 cm-1 at pH 6.0 and above 7). Tetrahexyldecyl ascorbate was assayed.

Inhibition of Mushroom Tyrosinase Activity: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) was incubated with its substrate L-Dopa (Fisher) in the presence or absence of vegetable amino acids. Pigment formation was evaluated by colorimetric plate reading at 490 nm. The percent inhibition of mushroom tyrosinase activity was calculated compared to non-treated controls to determine the ability of test ingredients or combinations thereof to inhibit the activity of purified enzyme. Test extract inhibition was compared with that of kojic acid (Sigma).

Increase of Collagen Stimulation: Collagen is an extracellular matrix protein critical for skin structure. Increased synthesis of collagen helps improve skin firmness and elasticity. This bioassay was used to examine the effect of tetrahexyldecyl ascorbate, and/or Phyllanthus emblica fruit extract on the production of procollagen peptide (a precursor to collagen) by human epidermal fibroblasts. The endpoint of this assay was a spectrophotometric measurement that reflects the presence of procollagen peptide and cellular viability. The assay employed the quantitative sandwich enzyme immunoassay technique whereby a monoclonal antibody specific for procollagen peptide had been pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color develops in proportion to the amount of procollagen peptide bound in the initial step using a microplate reader for detection at 450 nm. The color development was stopped and the intensity of the color was measured. For generation of samples and controls, subconfluent normal human adult epidermal fibroblasts (Cascade Biologics) cultivated in standard DMEM growth medium with 10% fetal bovine serum (Mediatech) at 37° C. in 10% $CO_2$, were treated with each of the ingredients for 3 days. Following incubation, cell culture medium was collected and the amount of procollagen peptide secretion quantified using a sandwich enzyme linked immuno-sorbant assay (ELISA) from Takara (#MK101).

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilized B16-F1 melanocytes (ATCC), an immortalized mouse melanoma cell line, to analyze the effect of the vegetable amino acids on melanogenesis. The endpoint of this assay was a spectrophotometric measurement of melanin production and cellular viability. B16-F1 melanocytes, were cultivated in standard DMEM growth medium with 10% fetal bovine serum (Mediatech) at 37° C. in 10% $CO_2$ and then treated with the vegetable amino acids of the topical skin composition for 6 days. Following incubation, melanin secretion was measured by absorbance at 405 nm and cellular viability was quantified.

Cyclooxygenase (COX) Assay: An in vitro cyclooxygenase-1 (COX-1) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measured the peroxidase component of cyclooxygenases. The peroxidase activity was assayed colorimetrically by monitoring the appearance of oxidized N,N,N',N'-tetramethyl-p-phenylenediamine (TMPD). This inhibitor screening assay included both COX-1 and COX-2 enzymes in order to screen isozyme-specific inhibitors. The Colormetric COX (ovine) Inhibitor screening assay (#760111, Cayman Chemical) was used to analyze the effects of Phyllanthus emblica fruit extract on the activity of purified cyclooxygnase enzyme (COX-1). According to manufacturer instructions, purified enzyme, heme and test extracts were mixed in assay buffer and incubated with shaking for 15 min at room temperature. Following incubation, arachidonic acid and colorimetric substrate were added to initiate the reaction. Color progression was evaluated by colorimetric plate reading at 590 nm. The percent inhibition of COX-1 activity was calculated compared to non-treated controls to determine the ability of Phyllanthus emblica fruit extract to inhibit the activity of purified enzyme.

Lysyl Oxidase Assay: Phyllanthus emblica fruit extract has been shown to increase lysyl oxidase expression. A lysyl oxidase assay was performed on skin cells (e.g., epidermal keratinocytes, fibroblasts, and/or dermal endothelial cells) to determine the ability of Phyllanthus emblica fruit extract to stimulate expression of lysyl oxidase in skin. Lysyl oxidase can catalyze crosslinking of elastin and collagens, thereby providing for a more structurally rigid matrix for skin. By increasing expression of lysyl oxidase, increased cross-linking of elastin and collagens can occur, which can be beneficial in reducing the appearance of fine lines, wrinkles, sagging skin, and/or non-elastic skin. It was determined that Phyllanthus emblica fruit extract increased lysyl oxidase expression by 40%.

Antioxidant (AO) Assay: An in vitro bioassay that measures the total anti-oxidant capacity of Phyllanthus emblica fruit extract. The assay relies on the ability of antioxidants in the sample to inhibit the oxidation of ABTS® (2,2'-azino-di-[3-ethylbenzthiazoline sulphonate]) to ABTS®·+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation was compared with that of Trolox, a water-soluble tocopherol analogue, and was quantified as molar Trolox equivalents. Anti-Oxidant capacity kit #709001 from Cayman Chemical (Ann Arbor, Mich. U.S.A.) was used as an in vitro bioassay to measure the total anti-oxidant capacity of Phyllanthus emblica fruit extract. The protocol was followed according to manufacturer recommendations. The assay relied on antioxidants in the sample to inhibit the oxidation of ABTS® (2,2'-azino-di-[3-ethylbenzthiazoline sulphonate]) to ABTS®·+ by metmyoglobin. The capacity of the antioxidants in the sample to prevent ABTS oxidation was compared with that Trolox, a water-soluble tocopherol analogue, and was quantified as a molar Trolox equivalent.

4. Example 4 (Clinical Study)

It has been determined that the combination of tetrahexyldecyl ascorbate, Phyllanthus emblica fruit extract, vegetable amino acids, tocopherol, and/or ascorbic acid, can reduce fine lines, wrinkles on skin, and improve skin firmness, skin elasticity, skin tone clarity, skin radiance and/or brightness, skin tone evenness, and/or overall skin appearance.

a. Evaluation of Anti-ageing Efficacy of Topical skin composition on Skin

Briefly, double-blind and controlled clinical studies were conducted on Asian female subjects between ages 30 to 65 having mild to moderate facial skin dullness, mild to moderate facial skin sagging and/or laxity, and/or mild to moderate facial wrinkles. In the study, which involved clinical expert grading, cutometer, full face digital image analysis, and 3D imaging analysis on wrinkles, 39 such subjects were tested. All the subjects applied the serum comprising combination of tetrahexyldecyl ascorbate, Phyllanthus emblica fruit extract, vegetable amino acids, tocopherol, and ascorbic acid, twice daily over their face and neck areas. Supplemental SPF 30 moisturizing sunscreen and were also provided to each subject for the entire study duration. For this study, 1 week washout period was applied followed by 8 weeks product usage.

Clinical expert provided grades for parameters including fine lines and wrinkles, skin firmness (visual), skin elasticity (touch), skin tone clarity, skin radiance and/or brightness, skin tone evenness, overall skin photo-damage and/or appearance. Cutometer was used to grade skin firmness and skin elasticity. A 3D imaging system (Primos Lite) was used to analyze average wrinkle depth, wrinkle volume, wrinkle area, length of wrinkles in the periorbital-crow's feet region of the subjects.

b. Results for Clinical Expert Grading

As shown in FIG. 1, the clinical expert grades indicate that, based on the mean percentage improvement for each parameter, after using the serum comprising combination of the aforementioned ingredients for 4 and 8 weeks, fine lines, wrinkles, skin firmness, skin elasticity, skin tone clarity, skin tone evenness, skin radiance and/or brightness, and overall skin photo-damage/appearance of the subjects were significantly improved.

As shown in Table 8, the results of the clinical expert grades on the percentage of panelist indicated improvement in each parameter. The results show that after 4 weeks of using the serum comprising the aforementioned active ingredients, over 50% of the panelist showed improvement in skin firmness, skin tone clarity, skin radiance and/or brightness, skin tone evenness, and overall skin appearance and/or photo damage. About 28% of the panelist showed improvement in fine lines, and about 17% of the panelist showed improvement in wrinkles after 4 weeks of using the aforementioned serum. The results further showed that after 8 weeks of using the serum, 92% of the panelist showed improvement in overall skin appearance and/or photo-damage. About 89% of panelist had visibly firmer skin after 8 weeks of using the serum. More than 70% of the panelist showed improvement in all the other expert graded parameters after 8 weeks of using the serum.

TABLE 8

Results from clinical expert grader

| Measured Attribute | Method | Percentage of Panelist Showed Improvement Relative to Baseline | |
|---|---|---|---|
| | | Week 4 | Week 8 |
| Fine lines | Clinical | 28% | 84% |
| wrinkles | Expert | 17% | 71% |
| Skin firmness (visual) | Grader | 51% | 89% |
| Skin elasticity (touch) | | 43% | 76% |
| Skin tone clarity) | | 58% | 82% |
| Skin radiance/ brightness | | 76% | 87% |
| Skin tone evenness | | 61% | 82% |
| Overall Appearance/ Photo-damage | | 76% | 92% |

Figure 2:
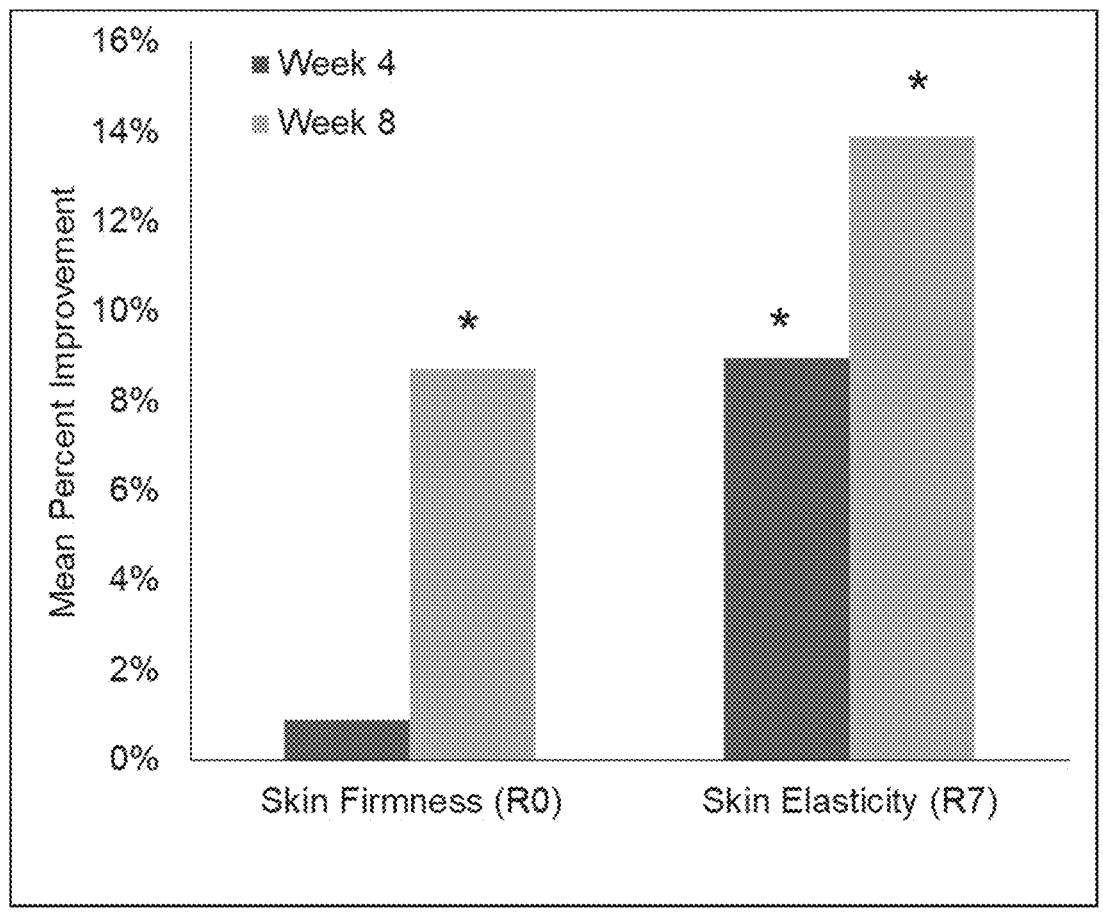
FIG. 2 shows the result of cutometer graded parameters including skin firmness and skin elasticity of tested subjects after using a serum comprising the combination of the skin active ingredients of the present invention for 4 and 8 weeks.

FIG. 2 shows the result of cutometer graded parameters including skin firmness and skin elasticity. The results show statistically significant improvement in skin firmness after 8 weeks of using the serum comprising the combination of the aforementioned ingredients. The elasticity of the subjects were also improved using the serum comprising the combination of the aforementioned ingredients for 4 and 8 weeks, according to FIG. 2.

Figure 3:
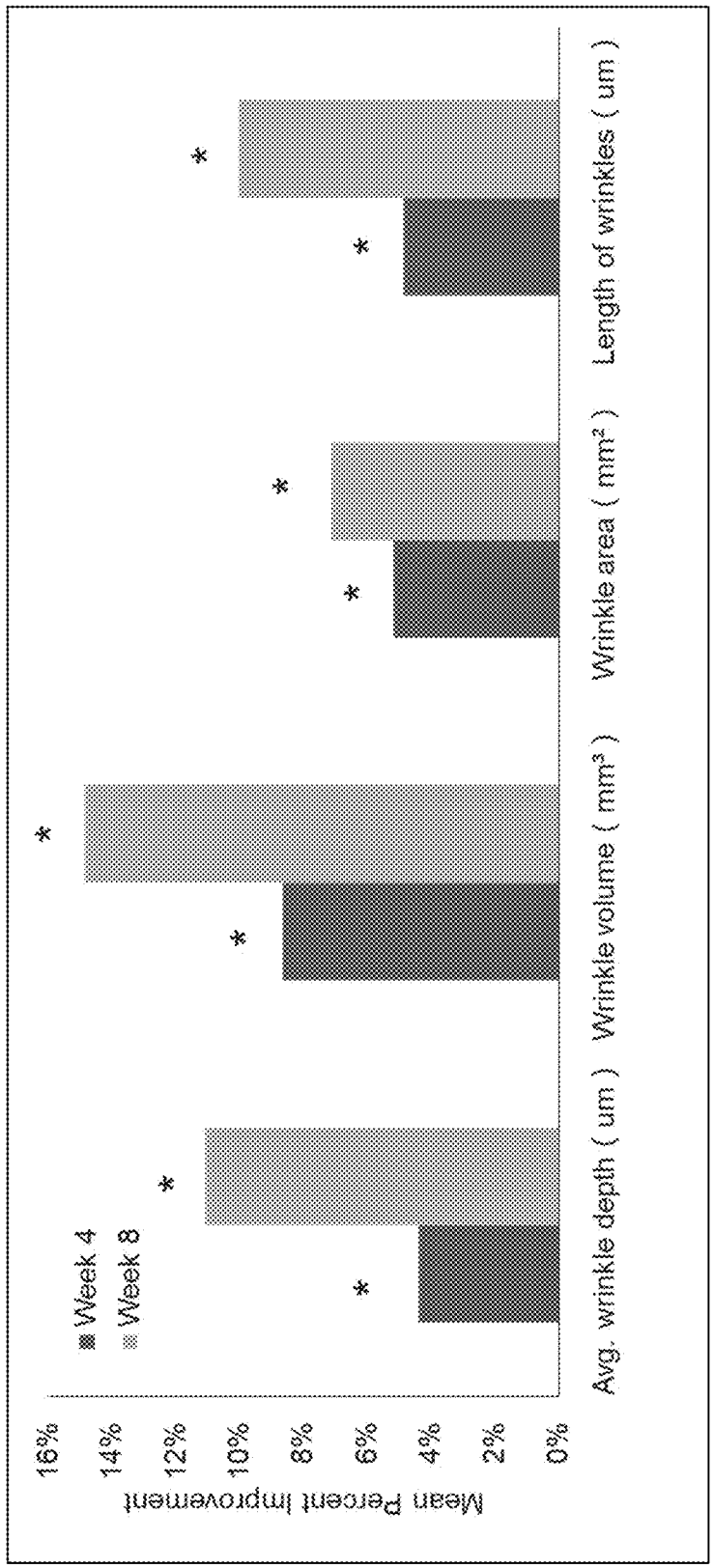
FIG. 3 shows the results for 3D image analysis for wrinkle depth, wrinkle volume, wrinkle area, and length of wrinkle of the subjects after using the serum comprising the combination of the skin active ingredients of the present invention for 4 and 8 weeks.

FIG. 3 shows the results (mean percentage of improvement) for 3D imaging analysis on average wrinkle depth, wrinkle volume, wrinkle area, length of wrinkles after 4 weeks and 8 weeks of using the serum comprising the aforementioned active ingredients. The results indicate that the after 4 weeks of using the serum, the average wrinkle depth was reduced by more than 4%, the wrinkle volume was reduced by more than 8%, the wrinkle area was reduced by more than 4%, and the length of wrinkles was reduced by more than 4%. After 8 weeks of using the serum, the average wrinkle depth was reduced by about 11%, the wrinkle volume was reduced by more than 15%, the wrinkle area was reduced by more than 7%, and the length of wrinkles was reduced by about 10%.

Table 9 shows the results of the cutometer analysis and the 3D imaging analysis on the percentage of panelist that showed improvement in each parameter including skin firmness, skin elasticity, average wrinkle depth, wrinkle volume, wrinkle area, and length of wrinkles. The results of cutometer analysis show that after 4 weeks of using the serum comprising the aforementioned active ingredients, about 51% of panelist showed improvement in skin firmness, 69% showed improvement in skin elasticity. After 8 weeks of using the serum, about 64% of panelist showed improvement in skin firmness, and 76% of panelist showed improvement in skin elasticity. The results of 3D imaging analysis showed that after 4 weeks of using the serum, 74% of panelist showed reduced average wrinkle depth, 87% of panelist showed reduced wrinkle volume, 66% of panelist showed reduced wrinkle area, and 71% of panelist showed reduced length of wrinkles. After 8 weeks of using the serum. About 89% of panelist showed reduced average wrinkle depth, 92% of panelist showed reduced wrinkle volume, about 84% of panelist showed reduced wrinkle area, and about 87% of panelist showed reduced length of wrinkles.

TABLE 9

Results of cutometer and 3D imaging analyses

| Measured Attribute | Method | Percentage of Panelist Showed Improvement Relative to Baseline | |
| --- | --- | --- | --- |
| | | Week 4 | Week 8 |
| Skin firmness | Cutometer | 51% | 64% |
| Skin Elasticity | | 69% | 76% |
| Average wrinkle depth | 3D Imaging analysis | 74% | 89% |
| Wrinkle volume | | 87% | 92% |
| Wrinkle area | | 66% | 84% |
| Length of wrinkles | | 71% | 87% |

5. Example 5 (Additional Assays that can be used to Test Compositions)

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin Stimulation Assay: Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ. Laminin secretion can be monitored by quantifying laminin in cell supernatants of cultured human fibroblasts treated for 3 days with culture medium with or without 1.0% final concentration of the test ingredient(s). Following incubation, laminin content can be measured using immunofluorescent antibodies directed against laminin in an enzyme linked immunosorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: EnzChek® Elastase Assay (Kit# E-12056) from Molecular Probes (Eugene, Oreg. U.S.A.) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$—Standardize roughness; $l_m$—the traverse (scan) length; and y—the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® Simon™ western blotting protocol. For each sample, normal human epidermal keratinocytes (NHEK) are grown in EPI-200—Mattek Epilife® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® Simon™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin—Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® Simon™ western blotting protocol. For the samples, adult human epidermal keratinocytes (HEKa) from Life Technologies (C-005-5C) can be grown at 37° C. and 5% CO2 for 24 hours in Epilife growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability =((Mean Ex/Em of test sample)/Mean Ex/Em untreated control)*100; Percent Change =Percent Permeability of test sample—Percent Permeability of untreated control.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol # EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity =(Inhibitor stopped wells absorbance at 600 nm—inhibitor reaction wells absorbance at 600 nm); Initial activity =control enzyme absorbance at 600 nm; Percent Inhibition =[(Initial activity/Inhibitor Activity)* 100]-100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EpiLife™ media (Cascade Biologics). The cells are seeded in 6-well plates at approximately 10-20% confluency. After the cells became approximately 80% confluent, the media is aspirated and 1.0 ml of EpiLife™, along with phorbol 13-Myristate 12-acetate ("PMA") (a known inducer of inflammation) and the test composition dilutions are added to two replicate wells (i.e., 1.0% (100 μl of 100X stock) and 0.1% (10 μl of 100X stock) test compositions are diluted into a final volume of 1 ml EpiLife Growth Medium). The media is gently swirled to ensure adequate mixing. In addition, 1.0 ml of EpiLife™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FAST Frame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

* * * * * * * * * * * * *

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of brightening a person's skin or evening skin tone, the method comprising applying to the person's skin an effective amount of a topical skin composition comprising:
Phyllanthus emblica fruit extract;
ascorbic acid;
tocopherol or tocopherol acetate;
glycerin;
dipotassium glycyrrhizate;
ferulic acid;
sodium hyaluronate;
pentylene glycol;
sorbic acid;
phenoxyethanol; and
ethylhexylglycerin,
wherein topical application of the composition to the person's skin brightens the skin or evens the person's skin tone.

2. The method of claim 1, wherein the skin has age spots.

3. The method of claim 1, wherein the composition reduces melanogenesis or tyrosinase activity in the skin.

4. The method of claim 1, wherein the topical skin composition is applied to facial skin.

5. The method of claim 1, wherein, after topical application, the topical skin composition remains on the skin for at least 30 minutes.

6. The method of claim 1, wherein the topical skin composition is applied one or more times daily for at least 4 weeks.

7. The method of claim 1, wherein the Phyllanthus emblica fruit extract is an aqueous extract from Phyllanthus emblica fruit.

8. The method of claim 1, wherein the skin is photo damaged skin.

9. The method of claim 1, wherein the skin has dark spots.

* * * * *